US010571351B2

(12) United States Patent
Forestelli et al.

(10) Patent No.: US 10,571,351 B2
(45) Date of Patent: Feb. 25, 2020

(54) GROUP AND METHOD FOR MEASURING THE PRESSURE IN CLOSED CONTAINERS

(71) Applicant: FT SYSTEM S.R.L., Alseno (IT)

(72) Inventors: Fabio Forestelli, Alseno (IT); Massimo Fedel, Padua (IT)

(73) Assignee: FT SYSTEM S.R.L., Alseno (IT)

( * ) Notice: Subject to any disclaimer, the term of this patent is extended or adjusted under 35 U.S.C. 154(b) by 399 days.

(21) Appl. No.: 15/515,905

(22) PCT Filed: Sep. 29, 2015

(86) PCT No.: PCT/IB2015/057454
§ 371 (c)(1),
(2) Date: Mar. 30, 2017

(87) PCT Pub. No.: WO2016/051341
PCT Pub. Date: Apr. 7, 2016

(65) Prior Publication Data
US 2017/0299455 A1    Oct. 19, 2017

(30) Foreign Application Priority Data

Sep. 30, 2014  (IT) .............................. MI2014A1703

(51) Int. Cl.
*G01L 11/02*  (2006.01)
*G01M 3/38*  (2006.01)
*G01N 21/39*  (2006.01)
*G01M 3/32*  (2006.01)
(Continued)

(52) U.S. Cl.
CPC ................ *G01L 11/02* (2013.01); *B67C 3/22* (2013.01); *B67C 7/0026* (2013.01);
(Continued)

(58) Field of Classification Search
CPC . G01L 11/02; G01L 19/0092; G01N 21/3504; G01N 21/39; G01N 21/31;
(Continued)

(56) References Cited

U.S. PATENT DOCUMENTS

| 3,966,323 A | 6/1976 | Matsuoka et al. |
| 4,549,809 A | 10/1985 | Minekane et al. |

(Continued)

FOREIGN PATENT DOCUMENTS

| EP | 2 620 761 A1 | 7/2013 |
| WO | 2009050177 A1 | 4/2009 |

(Continued)

OTHER PUBLICATIONS

Herman Koll, Written Opinion of the International Searching Authority with International Search Report, dated Jan. 19, 2016.

*Primary Examiner* — Hoa Q Pham
(74) *Attorney, Agent, or Firm* — Florek & Endres PLLC

(57) ABSTRACT

A group and method for measuring the pressure in closed containers made from optically transparent material at least at a portion of a top space without contacting the containers, and a filling and/or packaging plant using the measuring group. The measuring group comprises an inspection area; a laser source with optical axis for the emission of a laser beam at a wavelength tunable with an absorption wavelength of a gas contained in a container top space; at least one detector to detect the laser beam once it has travelled through the inspection area to provide an absorption spectrum of said gas; a device for detecting the signal acquisition time period corresponding to the passage of a top space through the inspection area; having means for identifying signal contributions useful for the pressure measurement amongst the data representative of an absorption spectrum acquired during the signal acquisition time period.

13 Claims, 5 Drawing Sheets

(51) Int. Cl.
  *B67C 3/22* (2006.01)
  *B67C 7/00* (2006.01)
  *G01L 19/00* (2006.01)
  *G01N 21/90* (2006.01)
(52) U.S. Cl.
  CPC ....... *G01L 19/0092* (2013.01); *G01M 3/3272* (2013.01); *G01M 3/38* (2013.01); *G01N 21/39* (2013.01); *G01N 21/90* (2013.01)
(58) Field of Classification Search
  CPC .... G01N 21/9504; G01N 21/90; G01N 33/14; G01M 3/3263; G01M 3/002; B67C 3/22; B67C 7/0026
  USPC .............................. 356/428–440, 246, 240.1
  See application file for complete search history.

(56) References Cited

U.S. PATENT DOCUMENTS

| | | | | |
|---|---|---|---|---|
| 5,614,718 | A * | 3/1997 | Brace ................. | G01N 21/3504 250/339.07 |
| 5,861,548 | A * | 1/1999 | Melvin, II ............. | G01L 11/04 73/49.3 |
| 7,385,703 | B2 * | 6/2008 | Berg ....................... | G01L 11/02 356/436 |
| 7,948,626 | B2 * | 5/2011 | Tondello ................. | G01L 11/02 356/432 |
| 8,707,790 | B2 * | 4/2014 | Baumann ................ | G01L 11/02 73/705 |
| 2005/0022603 | A1 | 2/2005 | Lehmann et al. | |
| 2005/0084974 | A1 | 4/2005 | Veale et al. | |
| 2007/0165230 | A1 * | 7/2007 | Berg ....................... | G01L 11/02 356/436 |
| 2010/0067012 | A1 | 3/2010 | Tondello et al. | |
| 2013/0199127 | A1 * | 8/2013 | Forestelli ................ | B65B 7/28 53/53 |
| 2016/0231301 | A1 * | 8/2016 | Falkenstein ......... | G01L 19/0092 |
| 2017/0254721 | A1 * | 9/2017 | Casari ................... | G01M 3/002 |

FOREIGN PATENT DOCUMENTS

| | | |
|---|---|---|
| WO | 2012001633 A2 | 1/2012 |
| WO | 2012107597 A2 | 8/2012 |

\* cited by examiner

GROUP AND METHOD FOR MEASURING THE PRESSURE IN CLOSED CONTAINERS

FIELD OF THE INVENTION

The present invention concerns a group and a method for measuring the pressure in closed containers, as well as an automatic filling and/or packaging plant using such a group.

In particular the present invention concerns a group and a method for contactlessly measuring the pressure in closed containers, able to be used directly in automatic filling and/or packaging plants operating at high speed, without the need to stop or slow down such plants.

In the present description, the expression "directly measures in line" is meant to indicate the possibility of carrying out the measurement on the containers without the need to take them from the line beforehand.

The invention concerns a group and a method for measuring the total and/or partial pressure in closed containers at least partially made from optically transparent material, in particular plastic or glass material, like for example but not exclusively bottles of wine, beer, water, fizzy and still drinks, containers of beverages in general, produced in automatic filling and/or packaging plants operating at high speed. Measurement of the partial pressure in closed containers means the measurement of the pressure referring to a specific gas of the mixture of gases contained in the closed container.

In filling and/or packaging plants in general of containers, an important check required is that of testing the internal pressure and/or the leaks of the containers after filling and closing. As well as checking the seal of the container, the measurement of the internal pressure is aimed at monitoring the production process and the systems of which it consists (filling and capping steps). This type of measurement has a substantial impact on quality control and food safety.

In particular, the internal pressure measured must be comprised between a minimum internal pressure threshold and a maximum internal pressure threshold. Otherwise, the container should be considered unsuitable and therefore to be discarded, since an inappropriate pressure level can be due to errors in the filling process of the container or a leak of the container itself, caused for example by a defect in the closing system or by a hole in the container.

BACKGROUND OF THE INVENTION

Currently, numerous measurement techniques are known, selected as a function of the type of container and/or content. For example, in order to verify the pressure and/or leaks inside flexible containers, there are machines that exert a light pressure on the walls of the containers themselves and measure by diffuse sensing the internal "counter-pressure" through pressure transducers or detect the increase in level of the content through a video camera or another optical detector. These machines, as well as being bulky and having a significant impact on the production lines, are influenced by the operating plant conditions.

Alternatively, it is known to carry out the pressure measurement inside filled and closed containers, through systems for measuring the acoustic response of the container itself. For example, in plants for producing beer in glass bottles with crown cap closure, the systems for measuring the pressure used measure the acoustic response in frequency of the cap, wherein the internal pressure and the frequency are linked to one another by a direct dependency relationship. Such a technique is, however, influenced by the repetitiveness of the closures, i.e., for the same internal pressure, there could be a difference in the measurement of the acoustic response in the case in which the closures carried out are not perfectly identical.

For the measurement of the pressure inside containers made at least partially from optically transparent material, in particular plastic, glass or another similar material, it is known that it is possible to use so-called laser spectroscopy measuring instruments.

In the present description and in the subsequent claims, the expression "at least partially optically transparent material" is meant to indicate a material with absorbency such as to allow a photoreceiver to be sensitive to an optical signal transmitted by a laser source and having an optical path passing through such a material.

For measuring the pressure inside containers, the laser spectroscopy measuring instruments detect the absorption of a laser beam of suitable wavelength shot into the top space of the closed container. For this purpose, the container is made from optically transparent material at least at its top space.

In the present description and in the subsequent claims, the expression "top space" is meant to indicate the area enclosed in the closed container, in which the filling material (for example liquid) is not present. In the case of a container arranged with the closure facing upwards, the top space is the area comprised between the free surface of the material present in the container and the closure (for example the cap) of the container.

Alternatively, in the case of an inverted container, the top space indicates the area comprised between the free surface of the material present in the container and the bottom of the container.

Laser spectroscopy makes it possible to reliably measure the total pressure and the partial pressure of a gas present along the optical path that a laser beam travels between its source and a sensor (for example a photoreceiver). Moreover, the measurements are influenced little by external factors like for example possible deformities in the closures, and they can be made without contact with the containers and with instruments that are not very bulky.

For the measurement of the total pressure, such a measurement technique is applicable to containers filled with any type of liquid. In particular, a different pressure (overpressure or underpressure) is detected with respect to a reference pressure.

In order to carry out a measurement of the total pressure and/or of the partial pressure of a given gas inside a container through laser spectroscopy, the wavelength of emission of the laser is varied in a range that comprises one or more absorption lines of the gas under examination present in the optical path: by measuring with a sensor the variation of the optical power striking it, it is possible to determine the absorption of the beam that has passed through the column of gas and therefore, knowing the geometry being passed through, it is possible to determine the amount of gas present.

TDLAS (Tuneable Diode Laser Absorption Spectroscopy) technology that uses solid state lasers of the semiconductor type and WMS (Wavelength Modulation Spectroscopy) technology are particularly suitable for industrial applications. In the case of TDLAS technology, the variation of the emission wavelength of the laser is obtained by modulating the supply current of the laser itself: the modulation can preferably have a triangular, sinusoidal or sawtooth wave. In this way, as well as a variation of the emission wavelength of the laser there is a corresponding variation of the power emitted.

For the specific use of the measurement of the pressure inside closed containers, it is preferable to choose lasers that mainly emit between the near and the medium infrared where many roto-vibrational lines of gas molecules of practical interest are located, like for example those of $O_2$, $H_2O$, $CO_2$ or in traces as very many species such as $CH_4$, NO, HCL, CO, $N_2O$ and so on. Moreover, it is preferable to use lasers capable of emitting a strictly monochromatic radiation, i.e. characterised by a line width comprised between 10-50 MHz, in order to be able to determine the shape of the molecular line(s) of the gases encountered along the optical path and work out, based on such a shape and in particular the widening of the line, the total and partial pressure of the gas.

The Applicant has observed that the laser spectroscopy measuring instruments currently directly used in filling and/or packaging plants require that, during measurement, the product remains stationary or moves at extremely slow speed (for example at most equal to a few metres per minute). Such measurers are for example used to measure the oxygen content in phials of lyophilised drugs in which the phials are moved through positioning or centering spacers, with step by step advancing mode of the product. Before carrying out the measurement, the advancing product is stopped, or at least slowed down, at an inspection area. An example of an apparatus of this type for checking the internal pressure of a gas in a closed container, through laser spectroscopy, is dealt with in document WO 2005/040753.

The Applicant has also observed that laser spectroscopy measuring instruments currently directly used in filling and/or packaging plants carry out the check of the internal pressure of containers with high optical quality walls, like for example phials for pharmaceutical products that have walls with a low and homogeneous thickness along the entire extension and homogeneous colouring (or no colouring).

The Applicant has found that laser spectroscopy measuring apparatuses known in the state of the art are difficult to use to directly measure, on line, the internal pressure of commercial containers, like for example bottles. Such containers are characterised both by poor optical quality that leads to an even substantial attenuation of the laser beam, and by dishomogeneity of such walls that contributes to high diffusion of the light and retroreflection of the radiation.

The Applicant has, indeed, observed that, since the laser light is strongly coherent, every contribution of reflected/diffused light causes etalon disturbances, i.e. spurious and variable modulations of the intensity due to the interference between coherent beams. Such disturbances are often the limiting element to the precision with which a measurement can be carried out directly in line according to laser spectroscopy technology in commercial containers.

In the present description and in the subsequent claims, the expression "commercial containers" means containers characterised by ample variability of the material of which they consist.

In the present description and in the subsequent claims, the expression "variability of the material that constitutes the container" means deformations or variations in thickness in the material of the containers to be inspected, due for example to the production process of the containers themselves (such as glass bottles), or variations in thickness in the point of measurement due to the structural characteristics of the containers, such as to presence of the threading or of the closing cap at the measurement point.

The Applicant has also found that laser spectroscopy measurers according to the state of the art do not allow operation at the high speeds of forward motion characteristic of filling and/or packaging plants of foods or beverages.

In the present description and in the subsequent claims, the expression "high speed of forward motion" means a speed of forward motion of the filling plant up to 120 metres/minute, corresponding to a production rate equal to 72,000 pieces/hour.

The Applicant has indeed observed that, in order to be able to extract the absorption profile of the gas object of the measurement from which to then obtain the pressure of the container, it would be better to carry out a high number of scans in wavelength on the absorption line of the gas object of the analysis for each container since the more scans are carried out the more effective the measurement is, considering that the average over many scans allows the precision of the measurement itself to be improved. In this way, the data measurement contributions from scans that are not useful tend to have a low influence on the overall measurement.

In the present description and in the subsequent claims, the expression "measurement contribution" means the signal detected following a scan in wavelength on the absorption line of the gas object of analysis.

In the present description and in the subsequent claims, the expression "pressure measurement" means the whole of a plurality of measurement contributions equal to the number of scans that the laser spectroscopy measurer is able to carry out during the acquisition period on a container.

In the present description and in the subsequent claims, the expression "signal acquisition time period" means the time period in which at least one portion of the container transits through an inspection area.

The Applicant has also found that at the characteristic speed of filling and/or packaging plants of beverages or foods the signal acquisition time period is less than 40 ms, making it possible to carry out, for each passing container, a much lower amount of scans in wavelength with respect to the static or substantially static case. With this, the overall measurement of the pressure is particularly sensitive to the variability of the material of the container and, in order to obtain the measurement, it is necessary to identify and eliminate the non-useful measurement contributions (for example the measurements carried out at dishomogeneities of the walls of the container), in order to be able to process only useful contributions, by useful contributions meaning the single scanning periods having the correct form on the receiver.

In particular, the systems used up to now for determining the signal acquisition time period cannot be used at the characteristic speeds of filling and/or packaging plants of beverages or foods. Generally, in order to determine the signal acquisition time period it is known to base it on the calculation of the position carried out through encoder and/or through suitable photocells that detect the entry of the container inside the measurement area. However, the calculation offered by the encoder is not able to provide a precise indication since the forward motion system can undergo delays with respect to the reference of the encoder or even the container could not be firmly constrained to the forward motion system and therefore undergo displacements during the conveying. Similarly, not even the addition of photocells is sufficient to offer the level of precision necessary in use at the characteristic speeds of filling and/or packaging plants of beverages or foods. Indeed, the photocells have an emission of the optical beam that is very wide with respect to the dimensions of the top space of the container. The use of photocells can therefore at most be of help in providing a rough indication of the passage of the container, but certainly not in determining the actual signal acquisition time period.

The problem forming the basis of the present invention is therefore that of making a measuring group of the pressure in closed containers that is able to provide precise, repeatable and reliable measurements even when applied directly in a commercial container filling plant operating at high speed.

In particular, the purpose of the present invention is to devise a measuring group of the pressure in closed containers that allows extremely precise detection of the signal acquisition time period.

In accordance with a first aspect thereof, the invention concerns a measuring group of the pressure in closed containers made from optically transparent material at least at a portion of a top space thereof, comprising
- at least one inspection area adapted for the passage of at least one portion of a top space of a closed container of such closed containers;
- at least one laser source with optical axis for the emission of a laser beam at a wavelength tunable to an absorption wavelength of a gas contained in the top space of the closed container, the at least one laser source being positioned so as to direct the laser beam towards the at least one inspection area;
- at least one detector positioned so as to detect at least one portion of the laser beam emitted by the laser source once it has passed through the inspection area and to provide in output data representative of an absorption spectrum of the gas that occurred in the inspection area;
- at least one device for detecting a signal acquisition time period corresponding to the transit of said at least one portion of a top space of a closed container through the inspection area;

characterised in that it comprises means for identifying useful contributions to the pressure measurement among the data representative of the absorption spectrum of the gases acquired inside the acquisition time period.

In order to measure the pressure inside closed containers for food use, the measuring group according to the invention uses laser spectroscopy detecting the absorption preferably on the lines of oxygen ($O_2$), of water vapour ($H_2O$) or of carbon dioxide ($CO_2$). The choice is in general carried out depending on the content: in fizzy beverages the absorption of carbon dioxide is detected, in beverages with no added carbon dioxide, it is more helpful to detect the absorption of water vapour, whereas the absorption of oxygen is useful for measuring possible leaks in containers for example containing solid materials.

Depending on the type of product contained in the closed containers, in a filling and/or packaging plant the containers are generally conveyed with speeds such as to reach a production rate up to 120,000 pieces/hour.

The Applicant has realised that in the case of high transit speeds of the containers or of the optically transparent portions of the top spaces of the containers, through the inspection area, it is important to precisely identify the useful or significant laser signal measurement contributions acquired, i.e. those relative to the inside of the top space of the container, in order to be able to distinguish them from the non-significant measurement contributions and determine the pressure measurement from only the significant measurement contributions.

For this purpose, the Applicant has realised the need to identify the actually useful measurement contributions through a correlation between the instantaneous position of the container and the contributions themselves. Indeed, determining the internal pressure based substantially only on significant measurement contributions makes it possible to achieve a high degree of precision, reliability and repeatability of measurement, even with a small number of measurement contributions available due to the high speed of forward motion of the container.

In accordance with a second aspect thereof, the invention concerns a method for measuring the pressure in closed containers made from optically transparent material at least at a portion of a top space thereof, comprising the steps consisting of:
- conveying at least one portion of a top space of a closed container of said closed containers towards an inspection area;
- emitting a laser beam at a wavelength tunable to an absorption wavelength of a gas contained in the top space of the closed container towards the at least one inspection area;
- detecting at least one portion of the laser beam passing through the inspection area and providing in output data representative of an absorption spectrum of the gas as a consequence of the passage of the laser beam through the inspection area;
- determining a signal acquisition time period corresponding to the transit of said at least one portion of a top space of a closed container through the inspection area;
- acquiring the data representative of the absorption spectrum of the gas detected during the signal acquisition time period;

characterised in that it comprises the step of identifying, among the data representative of the absorption spectrum of the gas acquired, the representative data useful for measuring the pressure and determining the pressure measurement based on the useful representative data.

Advantageously, the method for measuring the pressure in closed containers according to the invention achieves the technical effects described above in relation to the measuring group of the pressure in closed containers.

In accordance with a third aspect thereof, the invention concerns an automatic filling and/or packaging plant of closed containers made from optically transparent material at least at a portion of a top space thereof comprising
- conveying means adapted for moving a plurality of containers forwards along a forward motion path, along such a forward motion path there being, in succession
- a first station for filling the containers comprising a plurality of taps or filling valves, and
- a second station for sealing and/or capping the containers comprising a plurality of sealing and/or capping heads, characterised in that downstream of the second sealing and/or capping station with respect to the path of forward motion at least one above described measuring group of the pressure in closed containers is arranged.

Advantageously, the filling and/or packaging plant according to the invention achieves the technical effects described above in relation to the measuring group of the pressure in closed containers.

The present invention in at least one of the aforementioned aspects can have at least one of the following preferred characteristics; these can in particular be combined with each other as desired in order to satisfy specific application requirements.

Preferably, the means for identifying the useful contributions for the pressure measurement, comprise at least:
- an element for detecting a first and a second minimum point of a curve deriving from the envelope of intensity profiles of the data representative of the absorption spectrum of the gas acquired within the acquisition time period;
- an element for determining the distance between such first and second minimum point; and
- an element for defining a measurement sub-window contained between the first and the second minimum point and centred with respect to them, said measurement sub-window defining the whole of useful contributions for the pressure measurement.

Advantageously, the means for identifying useful contributions for the pressure measurement determine a compensation of possible shifts due for example to external factors such as translations of the container on the belt, poor vertical stability of the container, bumping on guides, dimensional tolerance of the containers and so on.

Within the signal acquisition time period, as illustrated in FIG. 6, the means for identifying useful contributions for the pressure measurement usefully define an acquisition sub-window in order to exclude the possible non-significant contributions, accidentally acquired during the acquisition time period due to the external factors listed above.

Preferably, the device for detecting an acquisition time period comprises at least one position sensor for detecting an instantaneous position of the containers.

In this way, based on the position of the container detected and knowing the speed of forward motion of the container (for example in the case of constant speed) it is possible to calculate, in a simple and quick manner, the moment at which the container and, in particular, its top space enters into the inspection area, determining the start of the useful acquisition time period.

More preferably, the at least one position sensor is arranged substantially at or close to an entry to the inspection area.

Such an embodiment proves even more advantageous, since the information regarding the speed of forward motion is superfluous for determining the entry of the top space of the container in the inspection area. Advantageously, determining the useful acquisition time period is therefore even simpler and quicker.

Preferably, the device for detecting an acquisition time period comprises an element for detecting the instantaneous speed of forward motion of the closed containers.

In this way, it is usefully possible to also taking into account instantaneous variations of the speed of forward motion of the container and calculate the useful acquisition time period in an even more precise manner.

Preferably, the measuring group comprises a load-bearing structure of the laser source and of the detector provided with mechanical adjustment elements adapted for modifying the positioning of the laser source and of the detector.

More preferably, the mechanical adjustment elements comprise an adjuster of the vertical position of the assembly consisting of the laser source and of the detector and/or an adjuster of the horizontal distance between the laser source and the detector.

The presence of adjustment elements that allow the positioning of the laser source to be modified and of the detector advantageously make it possible to modify the position and the dimensions of the inspection area, adapting it as a function of the dimensions and the geometry of the container in transit through it.

Preferably, upstream and/or downstream of the inspection area defined between the laser source and the detector, the measuring group comprises an entry channel and/or an exit channel configured so as to house at least the portions of container defining the respective top spaces in transit towards the inspection area and/or away from it.

Preferably, the entry and exit channels are each delimited by a protective wall shaped like an inverted "U", made from opaque material.

Advantageously, the protective walls prevent external light from altering the acquisition of the photodetector. This proves important particularly in the case of direct sunlight on the machine, since sunlight contains all wavelengths, therefore also that of interest.

Moreover, the protective walls have a containing effect of the dry air injected into the measuring area. This is particularly advantageous in the case of measurement of the pressure of water vapour, since the presence of the walls slows down the exchange of air from the outside towards the inside and vice-versa, hindering as much as possible the access of external humid air into the area of analysis. Such external humid air would otherwise determine background noise in the measurement.

Preferably, the measuring group comprises a first flushing device for injecting into the inspection area a gas different from the gas contained in the top space of the closed container.

More preferably, the first flushing device comprises a first pair of horizontal nozzles at the inspection area.

The Applicant has found that, if the gas under examination is also present outside of the container, it is necessary to consider that along the optical path of the laser beam molecules of gas not relevant for the measurement of the pressure are involved, since they are outside of the top space and possibly at a different concentration/pressure from the concentration/pressure of the internal gas.

This happens, for example, in the measurement of the internal pressure in plastic bottles filled with water that is not fizzy and added with nitrogen. For this application, laser spectroscopy reveals the pressure through a scan on the absorption line of the water vapour ($H_2O$), a gas usually present also outside the container.

Alternatively, this happens in the measurements based on the concentration of oxygen inside a container. For this purpose, nitrogen is advantageously blown into the inspection area to eliminate as much as possible the oxygen present outside the container.

Advantageously, by providing a flushing device of a gas different from that under examination, the gas analysed is blown away from the inspection area reducing or ideally totally eliminating the measurement signal contributions not relevant for determining the pressure inside the container.

More preferably, the measuring group comprises a second flushing device for injecting, upstream of the inspection area with respect to a direction of forward motion of the closed containers, a gas different from the gas contained in the top space of the closed container.

Even more preferably, the second flushing device comprises three exit nozzles of the flushed gas, of which a first vertical nozzle is arranged above an entry of the entry channel that leads to the inspection area and has a vertical emission direction, facing downwards, and a pair of second horizontal exit nozzles arranged at such an entry of the entry channel, with horizontal emission direction and one horizontal nozzle facing towards the other.

The Applicant has observed that the high speed of forward motion of the containers determines a drawing of the gas that is located around them. This leads to a partial elimination of the gas flushed at the inspection area, due to the movement of the containers, and therefore to incomplete elimination of the gas under examination in such an area.

The provision of a second flushing device, arranged upstream of the inspection area (with respect to the direction of forward motion of the containers) and substantially entering into such an area, determines a loading of the area around the top space of the container entering into the inspection area with a gas different from the one under examination that is drawn towards the inspection area due to the movement of the container. In this way a compensation of a possible partial elimination of the gas flushed directly in the inspection area by the first flushing device is obtained.

Preferably, the measuring group comprises a signal conditioning element connected downstream of the detector, the signal conditioning element being adapted for receiving single measurement signal contributions detected by the detector and processing each measurement signal contribution to extract an absorption line determined by the gas contained in the top space of the closed container.

More preferably, the means for identifying useful contributions for the pressure measurement are implemented in the signal conditioning element connected downstream of the detector.

More preferably, the signal conditioning element comprises at least one sub-element for identifying and varying the amplitude of the measurement signal contribution acquired as a function of input parameters.

The Applicant has realised that the use of a sub-element for identifying and varying the amplitude of the detected signal advantageously makes it possible to compensate for possible variations in amplitude of the signal contribution detected due to disturbance factors like for example deformations or irregularity of the container (for example if made from glass), the presence of foam, in the case of fizzy drinks or beer, or the presence of a droplet of nitrogen in the top space, in general used to increase the total pressure in a bottle of mineral water.

More preferably, the signal conditioning element comprises at least one sub-element for identifying and eliminating excessively distorted measurement signal contributions.

The Applicant has observed that the laser signal on the receiver is very variable based on the application and the different operating conditions. For example, in the measurement of pressure inside glass bottles filled with beer, where the laser spectroscopy technique reveals the total and partial pressure of carbon dioxide, there are great distortions on the signal acquired caused by possible deformations of the glass or by the presence of foam in the product.

Similarly, in the measurement of pressure inside plastic bottles filled with still water, where the laser spectroscopy technique reveals the total pressure through scanning on the absorption line of water vapour, the presence of a droplet of nitrogen in the top space, used to increase the total pressure of the sealed bottle, causes great distortions of the detected signal (very variable presence of state of condensation as a function of the time passed since the nitrogen was inserted and the amount thereof).

The measurement signal contributions therefore cannot all be used to determine the total pressure, so that an analysis of such contributions in order to discard the excessively distorted contributions is particularly useful, particularly in the case of a small amount of measurement contributions due to the high speed of forward motion of the containers.

More preferably, the signal conditioning element comprises at least one sub-element for weighing the single measurement signal contributions as a function of the length of the optical paths of the travelled by the laser beam through the top space.

The Applicant has considered that, as shown in FIG. 7, the optical paths of passage of the laser beam through the top space of a container, have, for every measurement contribution, a length that varies as a function of the shape of the top space. Purely as an example, the top space illustrated in FIG. 7 has a circular section.

The different length of the single optical paths relative to the single measurement contributions determines the fact that each measurement contribution is relative to a different number of molecules of gas analysed, since the number of molecules involved in the single optical paths is different.

Advantageously, the sub-element for weighing the single measurement signal contributions takes into account this effect that would otherwise introduce a non-negligible measurement error.

More preferably, the signal conditioning element comprises at least one sub-element for compensating a contribution of gas present outside the closed container, adapted for subtracting a direct measurement of the external gas from the at least one measurement signal contribution.

The Applicant has found that, in order to eliminate the measurement error determined by the presence of the gas under examination also outside the container it is possible, in addition or as an alternative to the flushing means, to provide a suitable compensating sub-element that subtracts a measurement carried out in the absence of the container from the measurement contributions, as schematised in FIG. 8.

In this way, it is usefully possible to eliminate the contributions due to the gas outside the container, obtaining a measurement relative exclusively to the gas present in the container.

Preferably, the step of identifying, among the data representative of the absorption spectrum of the gas acquired, the useful contributions for the measurement of the pressure comprises:
  detecting a first and a second minimum point of a curve deriving from the envelope of intensity profiles of the data representative of the absorption spectrum of the gas acquired within the acquisition time period;
  determining the distance between such first and second minimum point; and
  defining a measurement sub-window contained between the first and the second minimum point and centred with respect to them, the measurement sub-window defining the set of useful contributions for the pressure measurement.

Advantageously, in this way, among the measurement contributions detected during the useful acquisition time period, those actually relating to the inside of the top space of the closed container are identified, in this way compensating for possible shifts due for example to external factors such as translations of the container on the belt, poor vertical stability of the container, bumping on guides, dimensional tolerance of the containers and so on.

Preferably, the step of determining the signal acquisition time period comprises receiving at least one item of position data of the container detected through a position sensor and calculating the moment of entry of the top space of the closed container into the inspection area based on the at least one item of position data received.

In this way, based on the position of the container detected and knowing the speed of forward motion of the container (for example in the case of constant speed) it is possible to calculate, in a quick and simple manner, the moment at which the container and, in particular, its top space enters into the inspection area, determining the start of the acquisition time period.

Preferably, the step of determining the signal acquisition time period comprises receiving a plurality of items of instantaneous speed of forward motion data of the container and calculating the moment of entry of the top space of the closed container in the inspection area based on the plurality of items of instantaneous speed of forward motion data received.

In this way, it is usefully possible to also take into account instantaneous variations of the speed of forward motion of the container and finely calculate the useful acquisition time period.

Preferably, the measurement method comprises a step of blowing a different gas with respect to the one object of measurement against a container in transit in the inspection area.

Advantageously, foreseeing to blow a different gas with respect to the one object of measurement against a container in transit in the inspection area makes it possible to eliminate the gas under examination from the area around the container, reducing or ideally completely eliminating the measurement signal contributions not relevant to determining the pressure inside the container since they are relative to the gas outside the container.

Preferably, the measurement method comprises a step of a blowing a different gas with respect to the one object of measurement against a container entering into the inspection area.

Foreseeing to blow a different gas with respect to the one under examination against the container, when the container is entering into the inspection area, usefully determines a drawing of such a gas towards the inspection area due to the movement of the container. Thus, advantageously, the gas under examination present in the inspection area is pushed away.

Preferably, the step of providing in output an item of data representative of an absorption spectrum of the gas comprises:

identifying a characteristic background function of the measurement conditions of the signal detected;

subtracting such a background function from the signal detected and extracting an absorption line from the signal resulting from the subtraction.

Such conditioning of the detected signal is particularly advantageous since it makes it possible to eliminate the noise and the intrinsic disturbances of the measurement, isolating the portion of the detected signal that contains the information concerning the absorption that has occurred, based on which to precisely determine the pressure inside the container.

Preferably, the step of providing in output an item of data representative of an absorption spectrum of the gas comprises compensating for the variations in amplitude of the detected signal by varying the amplitude of the detected signal as a function of the material of the container and/or the type of gas object of measurement.

A low signal amplitude is, indeed, usually due to disturbance factors such as the presence of external or internal droplets, defects in the wall of the container, the presence of a tab that allows the product to be opened present in certain types of containers and so on. Such factors generally determine great attenuation of the signal.

Advantageously, the measurement method according to the present invention foresees to take into account the attenuation introduced by such disturbance factors compensating it in a suitable and specific manner for the single applications.

Preferably, the step of providing in output an item of data representative of an absorption spectrum of the gas comprises identifying and eliminating excessively distorted detected signals.

The identification and elimination of the excessively distorted measurement signals is particularly useful, particularly in the case of a small amount of measurement contributions due to the high speed of forward motion of the containers. In this case, using only significant measurement signals, the overall measurement is more precise and accurate.

More preferably, the step of identifying and eliminating distorted detected signals comprises verifying whether the amplitude of the absorption line is below an amplitude threshold.

More preferably, the amplitude threshold is variable as a function of the material of the container and/or the type of gas object of measurement.

Preferably, the step of identifying and eliminating distorted detected signals comprises checking whether the angular coefficient or slope of the rising front of the detected signal is outside of a range of angular coefficients or slopes considered admissible.

Each signal transmitted by the laser source has, indeed, a known shape given by the modulation of the laser, for example triangular wave, sawtooth, square wave and so on. Starting from a measurement parameter of the known shape, like for example the angular coefficient or slope of the rising front in the case of a triangular or sawtooth wave, it is possible to identify an excessive distortion of the corresponding output signal, carrying out a comparison between the parameter of the signal detected with that of the known shape.

If the parameter of the detected signal diverges excessively from the parameter of the known shape, the detected signal is discarded.

Preferably, the step of identifying and eliminating distorted detected signals comprises checking an asymmetry of the rising front with the descending front, in the case of signals emitted by the laser source modulated with a triangular wave, and discarding signals having an asymmetry greater than an asymmetry threshold considered admissible.

Preferably, the step of identifying and eliminating distorted detected signals comprises checking a duty cycle percentage of the detected signal and discarding signals having a duty cycle percentage outside of a range of duty cycle percentages considered admissible.

Such a check is particularly useful in the case of modulations of the laser with a square wave.

Preferably, the step of providing in output an item of data representative of an absorption spectrum of the gas comprises weighing the detected signal as a function of the length of the optical path travelled by the laser beam through the top space.

This makes it possible to achieve the advantageous effects outlined above relative to the use of the sub-element for weighing the single measurement signal contributions described above.

Preferably, the step of providing in output an item of data representative of an absorption spectrum of the gas comprises carrying out a direct measurement of the gas object of measurement in the absence of a container and subtracting such a direct measurement from the detected signal.

In this way, it is usefully possible to eliminate the contributions due to the gas outside the container, obtaining a measurement relative exclusively to the gas present in the container.

More preferably, the direct measurement is weighed as a function of the size of the top space.

More preferably, the weighing of the direct measurement is carried out as a function of the average length of the external optical path travelled by the laser beam.

Preferably, the measurement method comprises the step of determining a pressure measurement from a weighted average of a plurality of signals detected during the useful acquisition time period and in particular of the representative data identified as useful for the measurement of the pressure.

Alternatively, the measurement method comprises the step of determining a pressure measurement through absorption spectroscopy with WMS technology determining the distance of the minimum points of the second derivative of the absorption profile.

Advantageously, in this way a measurement of the total pressure is obtained that is independent of the optical path that is particularly useful in the case of ovalisation of the top space of the container.

According to a further alternative, the measurement method comprises the step of determining a pressure measurement through absorption spectroscopy with WMS technology determining the area of the absorption profile obtained from the second derivative of the absorption profile.

In a particularly advantageous manner, in the case of measurement of water vapour, the measurement of the area of the absorption profile provides a parameter proportional to the temperature of the container, in this way allowing a pressure measurement related to a known temperature to be obtained. Indeed, in a closed container containing a liquid with prevalence $H_2O$, the top space goes quickly into saturation (relative humidity 100%), whereas the concentration of the water vapour is directly proportional to the temperature of the liquid. Thanks to this proportion, a measurement of the area of the absorption profile makes it possible to have a parameter directly proportional to the temperature of the liquid.

BRIEF DESCRIPTION OF THE DRAWINGS

Further characteristics and advantages of the present invention will become clearer from the following detailed description of some preferred embodiments thereof, made with reference to the attached drawings.

The different characteristics in the single configurations can be combined together as desired according to the previous description, if it needs to have advantages resulting specifically from a particular combination.

Figure 1:
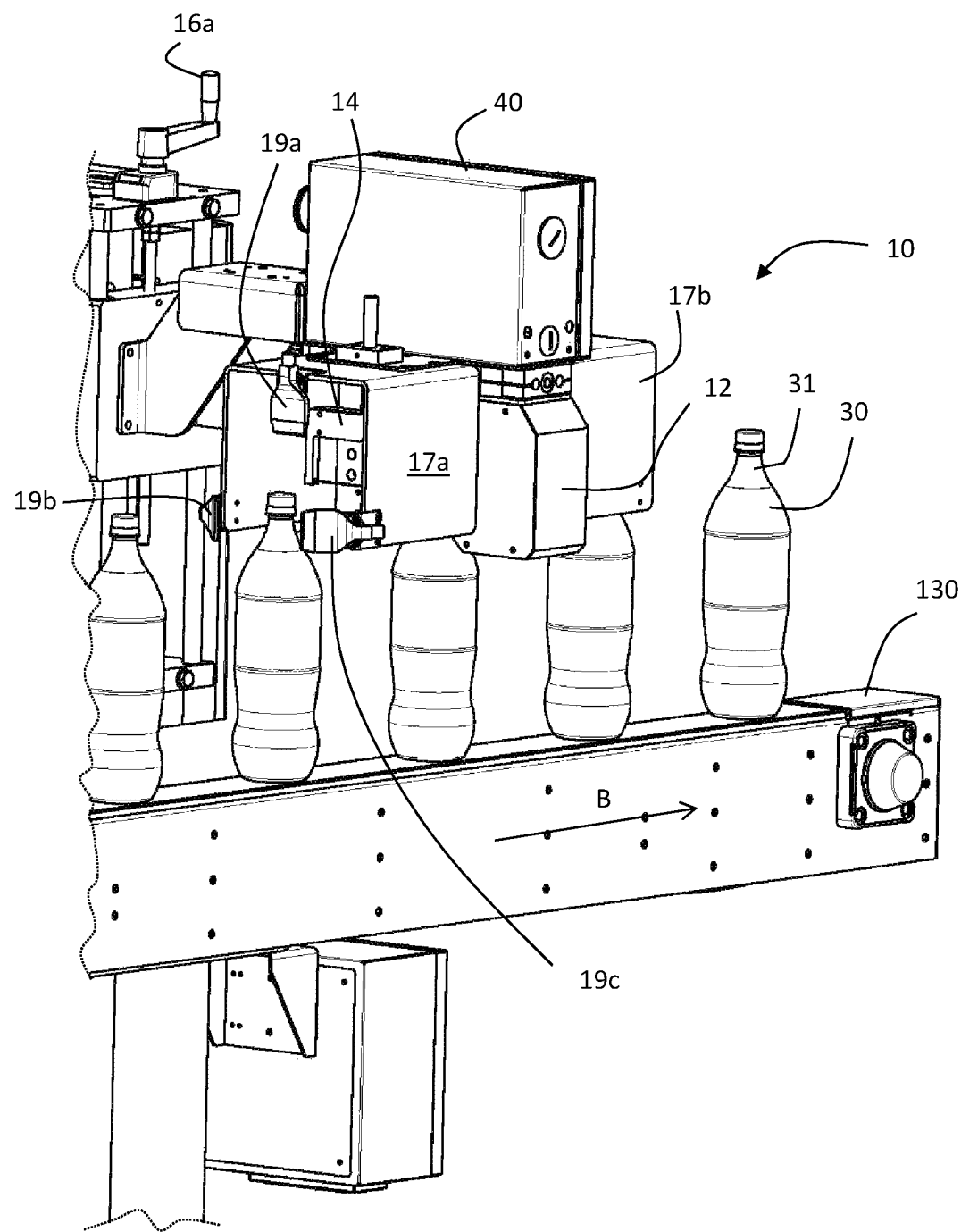
Figure 2:
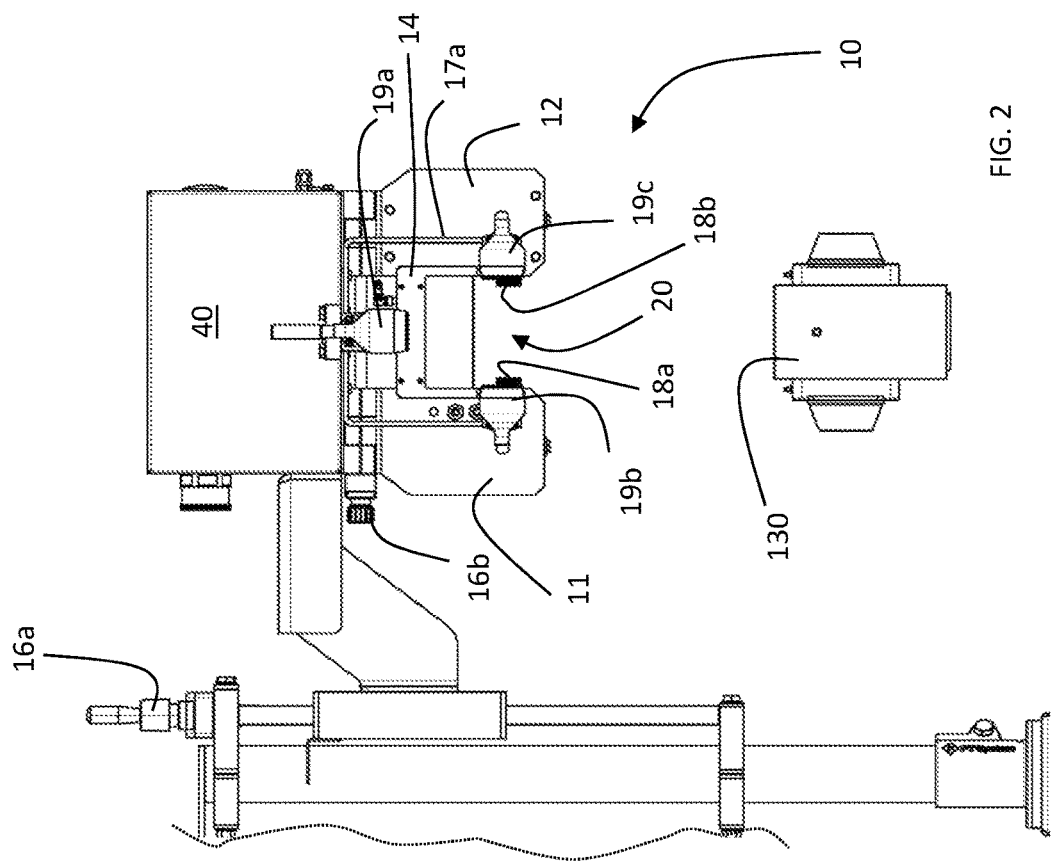
Figure 1A:
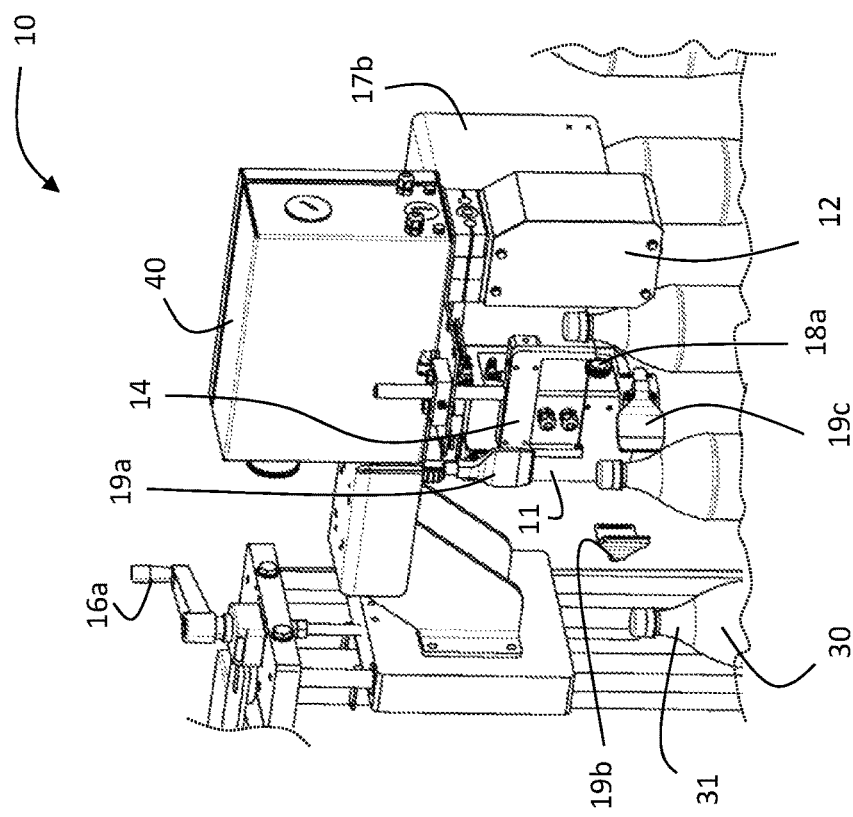
Figure 3:
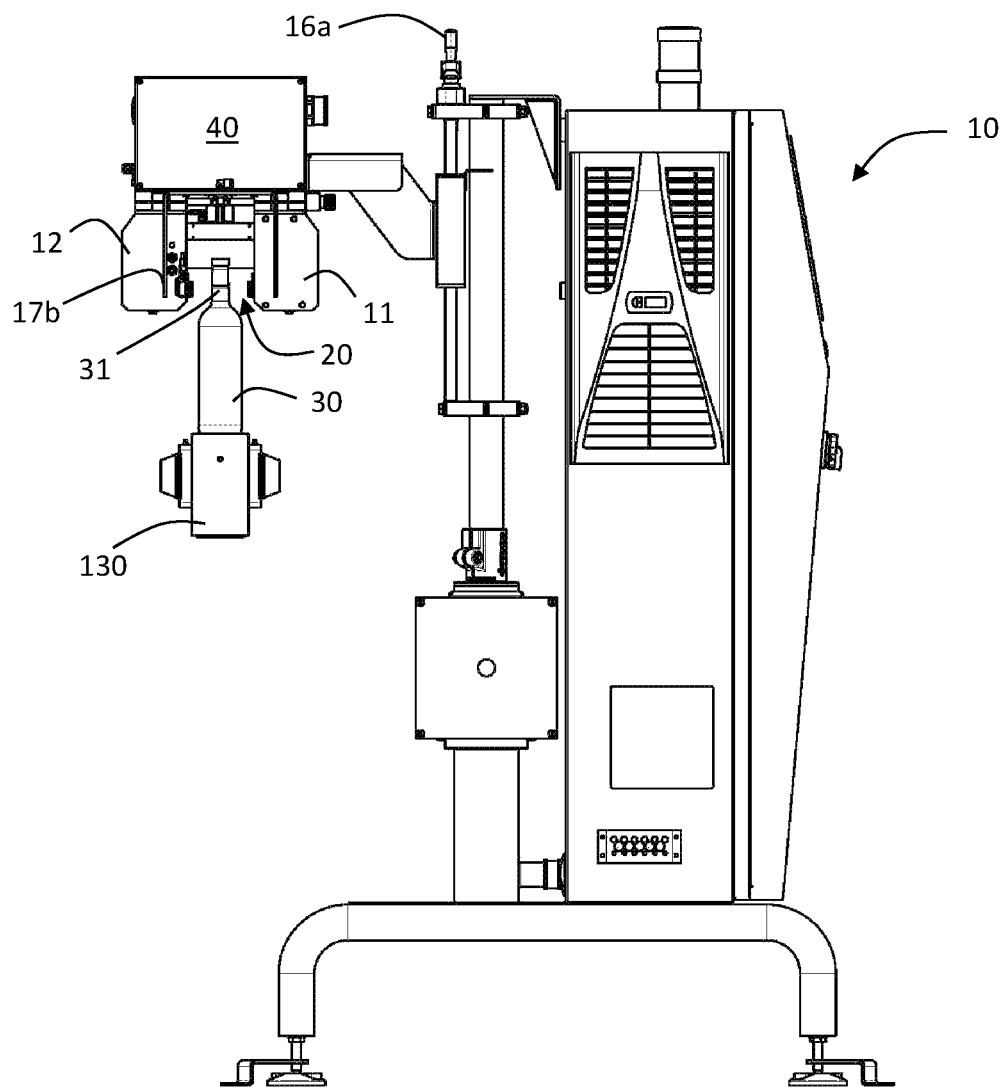
Figure 4:
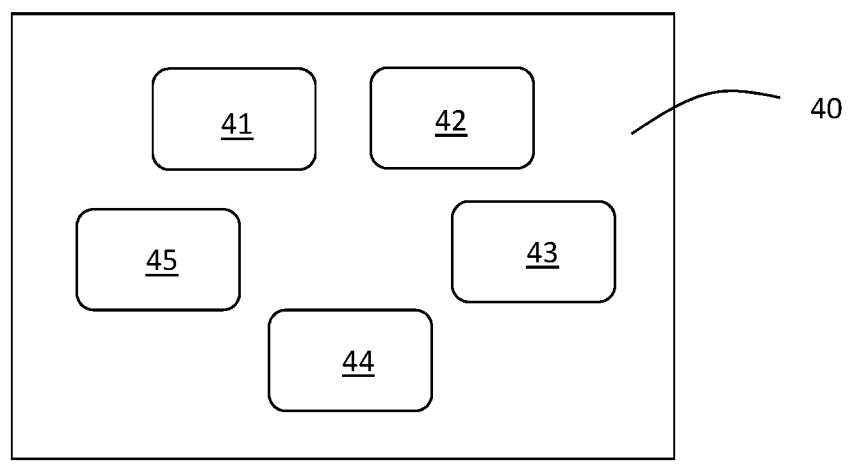
Figure 5:
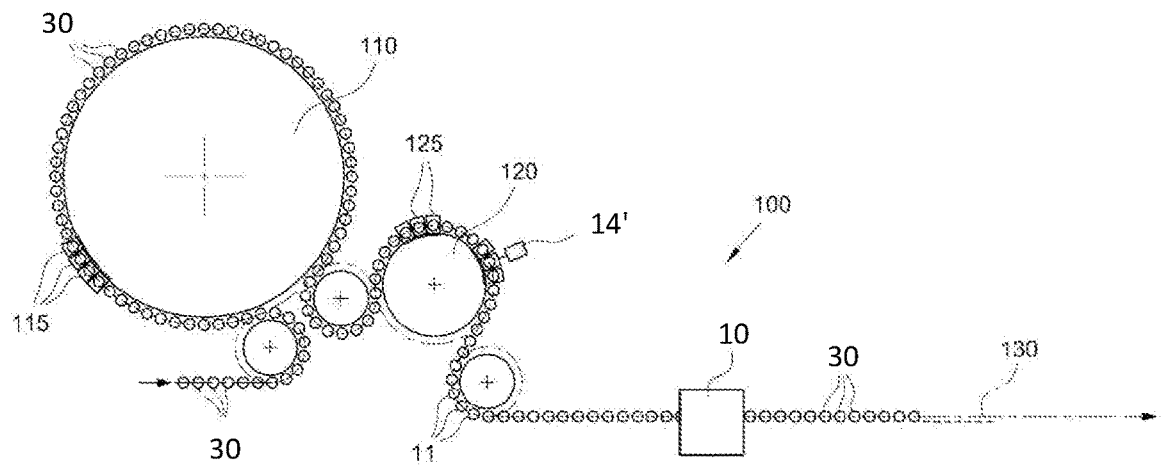
Figure 6:
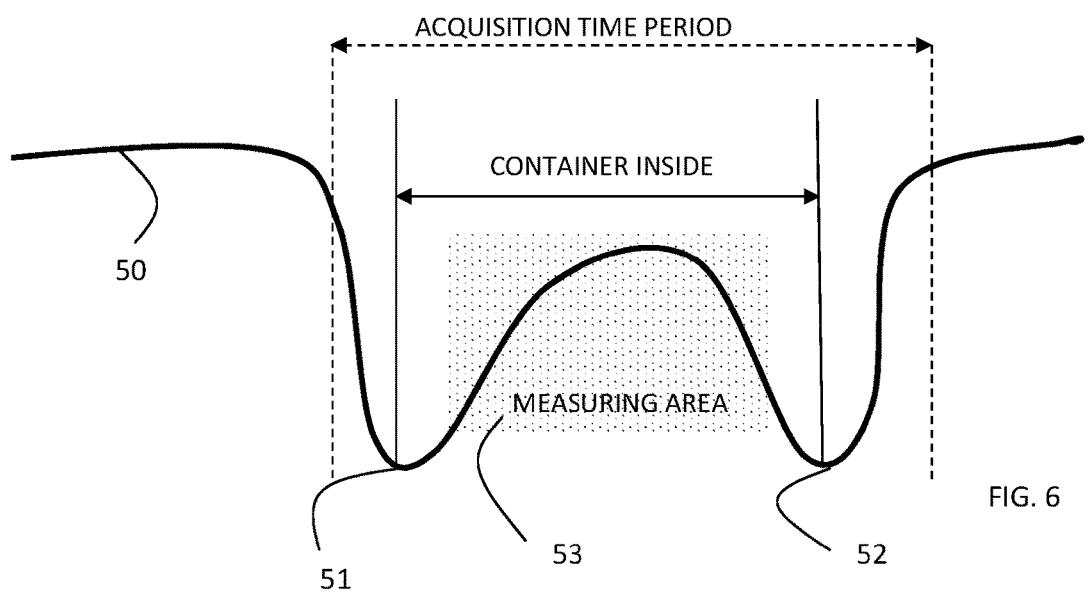
Figure 7:
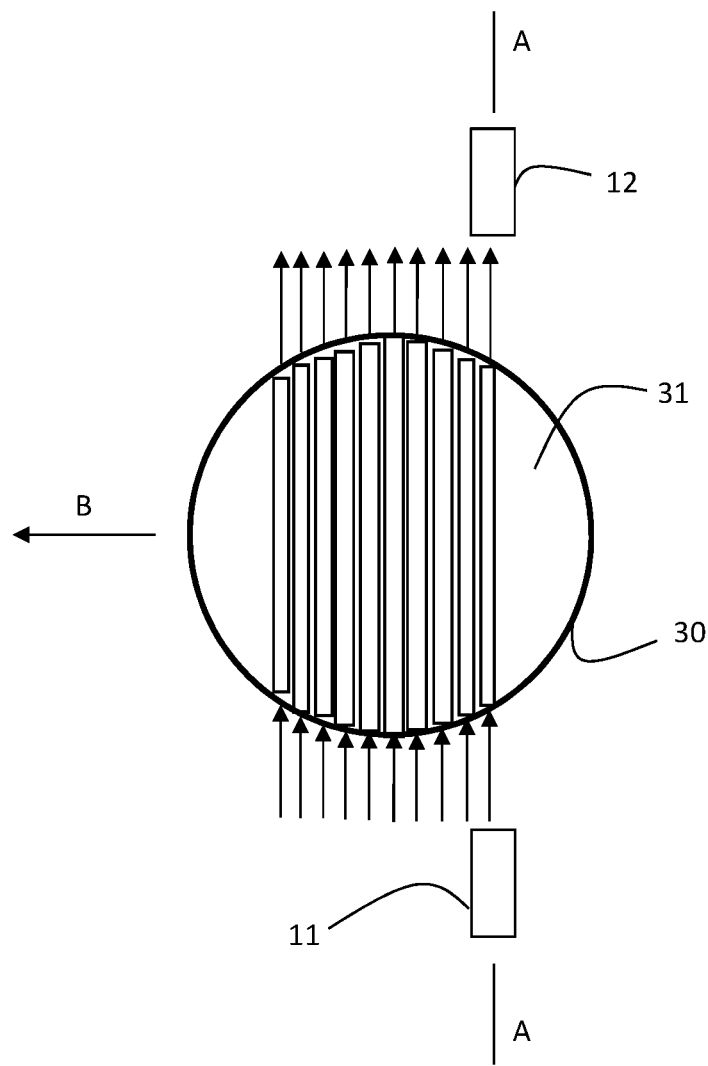
Figure 8:
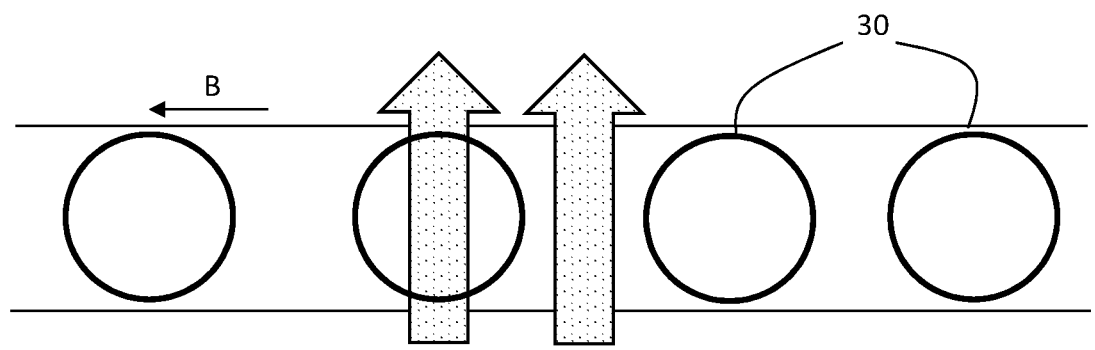

In such drawings,

FIG. 1 is a partial perspective view of an embodiment of the group for measuring the pressure in closed containers according to the present invention applied to a bottle filling plant;

FIG. 1*a* is an enlarged detail in a partially removed configuration of the measuring group of FIG. 1;

FIG. 2 is a partial front view of the measuring group of FIG. 1;

FIG. 3 is a rear view of the measuring group of FIG. 1;

FIG. 4 is a block diagram of the conditioning element of the signal used in the measuring group according to the invention;

FIG. 5 is a schematic representation of a filling and/or packaging plant according to the present invention;

FIG. 6 is a graphical representation of a measurement signal contribution acquired by the detector of the measuring group according to the present invention;

FIG. 7 is a schematic representation of a plurality of measurement contributions carried out during the passage of a container inside the measuring group of the invention;

FIG. 8 is a graphical representation of a conveyor belt of a plurality of containers at a measuring group according to the present invention.

DETAILED DESCRIPTION OF THE PREFERRED EMBODIMENT

In the following description, for the illustration of the figures, identical reference numerals will be used to indicate constructive elements with the same function. Moreover, for the sake of clarity of illustration, some reference numerals are not repeated in all of the figures.

With reference to the figures, a group for measuring the pressure in closed containers is shown, wholly indicated with 10.

In the present description and in the subsequent claims, it is presumed that the closed containers 30 subjected to checking are made from optically transparent material at least at a portion of its top space 31.

As shown in FIG. 1, the measuring group 10 comprises a laser source 11 having an optical axis A for emitting a laser beam and a detector 12 facing the laser source 11 so as to detect at least one portion of the laser beam emitted by the source 11.

In the space located between the laser source 11 and the detector 12 there is an inspection area 20 adapted for the passage of at least part of a closed container 30 and, in particular, of a top space 31 of the container 30 or, more specifically, of the portion of the top space 31 made from optically transparent material.

The laser source 11 is thus positioned so as to direct the laser beam towards the inspection area 20, therefore reaching the optically transparent portion of the top space 31 of a container 30 in transit through such an inspection area 20.

The laser source 11 is adapted for emitting a laser beam at a wavelength tunable with an absorption wavelength of a gas contained in the top space 31 of the closed container 30. The detector 12 is adapted for receiving the laser beam attenuated following the absorption that took place at the top space 31 of the container 30 in transit through the inspection area 20 due to the presence of the gas contained in the top space 31 and providing in output an item of data representative of an absorption spectrum of such a gas. In this way, it is possible to determine the pressure inside the closed container 30 as a function of the amplitude of the absorption line of such a gas.

The measuring group 10 also comprises at least one device 14,14' for detecting a signal acquisition time period. The device 14,14' for detecting the signal acquisition time period determines the time period of passage of the portion of top space 31 of the closed container 30 at the inspection area 20.

The device 14,14' for detecting the signal acquisition time period comprises at least one sensor 14,14' for detecting the position of the container 30, preferably at least one sensor for identifying the container 30 entering into the inspection area 20, like for example a photocell (illustrated in FIGS. 1-3) and/or an encoder (illustrated in FIG. 5), for example associated with an element for detecting the instantaneous speed of forward motion of the containers 30 through the inspection area 20.

In the case in which the containers 30 are conveyed through conveying means 130 of a filling and/or packaging plant 100, the element for detecting the speed of forward motion of the containers 30 is preferably a data input interface adapted for receiving data relative to the instantaneous speed of forward motion of the conveying means 130 of the filling and/or packaging plant 100.

Knowing the moment at which the top space 31 of the container 30 enters into the inspection area 20, the dimensions of such a top space 31 of the container 30 and the instantaneous speed of forward motion of the containers 30 it is possible to identify the time period in which the laser beam emitted by the laser source 11 passes through the top space 31 of the container 30, also in the case of instantaneous variations of the speed of forward motion. In this way, the useful signal acquisition time period is identified.

In the embodiment illustrated in FIGS. 1-3, the device for detecting the signal acquisition time period comprises a photocell 14 shaped like an inverted "U" and arranged at the entry to the inspection area 20 and the element for detecting the speed of forward motion is a data input interface (not illustrated) for receiving data relative to such a speed.

In the embodiment illustrated in FIG. 5, the device for detecting the signal acquisition time period comprises an encoder 14' arranged along the path carried out by the conveying means 130 and the element for detecting the speed of forward motion is a data input interface (not illustrated) for receiving data relative to such a speed.

According to an alternative embodiment that is not illustrated, preferably applicable in the case of constant speed of the conveyor belt, the device 14,14' for detecting the signal acquisition time period comprises at least one sensor for detecting the position of the container 30 (for example at least one photocell). In this case, it is superfluous to provide an element for detecting the speed of the conveyor belt since it is constant.

Also in this case it is possible to identify the time period in which the laser beam emitted by the laser source 11 passes through the top space 31 of the container 30 (signal acquisition time period) based on the distance between the point at which the sensor 14,14' intercepts the container 30 and the inspection area 20, the constant speed of the conveyor belt and the dimensions of the top space 31.

The measuring group 10 comprises, according to the illustrated embodiment, a load-bearing structure 15 for the correct positioning of the laser source 11 and of the detector 12, as well as the appropriate definition of the inspection area 20.

For this purpose, the load-bearing structure 15 comprises mechanical adjustment elements 16a,16b adapted for modifying the relative positioning of the laser source 11 and of the detector 12 as a function of the dimensions and the geometry of the container 30 in transit through the inspection area 20.

In the illustrated embodiment, the mechanical adjustment elements 16a,16b comprise an adjuster of the vertical position 16a of the assembly consisting of the laser source 11 and the detector 12 and an adjuster 16b of the horizontal distance between the laser source 11 and the detector 12 that allows them to be brought together and apart. The mechanical adjustment elements 16a,16b can be of the manual or motorised type.

Upstream and/or downstream of the inspection area 20 defined between the laser source 11 and the detector 12 there are preferably, respectively, an entry channel 17a and/or an exit channel 17b configured so as to house at least the portions of container 30 defining the respective top spaces 31 in transit towards the inspection area 20 or moving away from it 20.

For example, in the illustrated embodiment, the entry and exit channels 17a, 17b are made by means of a protective wall bent in a "U" and open towards the bottom. Such a protective wall is preferably made from a material not permeable to light.

As illustrated in FIG. 2, the measuring group 10 comprises a first flushing device 18a,18b for injecting into the inspection area a gas different from the one under examination. This makes it possible to reduce or eliminate the molecular absorption contribution given by the gas under examination present outside the container 30 and therefore the influence on the overall measurement.

The first flushing device comprises a first pair of horizontal nozzles 18a,18b a first of which 18a is integrated in the emission channel of the laser source 11 and a second 18b is integrated in the receiving channel of the detector 12 so that the flushing engages the entire path of the laser.

According to the particularly advantageous embodiment illustrated, the measuring group 10 preferably comprises in addition a second flushing device 19a,19b,19c arranged upstream of the inspection area 20 with respect to the direction B of forward motion of the containers. Such a second flushing device 19a,19b,19c loads the area around the top space 31 of the container 30 entering in with a gas different from the one under examination before such a top space 31 enters into the inspection area 20. The movement of the container 30 determines a drawing of the gas flushed towards the inspection area 20, compensating for a possible partial elimination of the gas flushed directly in such an area 20 by the first flushing device 18a,18b.

The second flushing device comprises three exit nozzles 19a,19b,19c of the flushed gas a first vertical nozzle 19a of which is arranged above the entry of the entry channel 17a that leads to the inspection area and has a vertical emission direction, facing downwards, and a pair of second horizontal exit nozzles 19b,19c arranged at such an entry of the entry channel 17a, with horizontal emission direction and facing one 19b towards the other 19c.

In order to obtain a valid measurement of the pressure inside each container 30 in transit from the single measurement contributions detected by the detector 12 during the signal acquisition time period, the measuring group 10 comprises means 41 for identifying signal contributions useful for the pressure measurement among the data representative of the absorption spectrum of the gas acquired within the acquisition time period, connected downstream of the detector 12.

Once the acquisition time period has been determined, the signals acquired by the detector 12 in such a time period are provided to the means 41 for identifying signal contributions useful for the pressure measurement. Such means 41 are adapted for analysing in real time the signal acquired by the detector 12 in order to isolate the significant signal contributions for the measurement, i.e. those actually corresponding to measurements carried out when the top space transits between the laser source 11 and the detector 12.

For this purpose, the means 41 for identifying signal contributions useful for the pressure measurement comprise at least:

- an element for detecting the minimum points 51,52 of a curve deriving from the envelope 50 of the intensity profiles of the data representative of the absorption spectrum of the gas acquired within the acquisition time period identified by the corresponding detection device 14,14',
- an element for determining the distance between such minimum points 51,52 and
- an element for defining a sub-window 53 contained between the minimum points 51,52 and centred with respect to them. The sub-window centred with respect to the minimum points 51,52 detected actually defines the set of contributions actually useful for the pressure measurement.

The envelope 50 of the intensity profiles of the signals that passed through a bottle is illustrated as an example in FIG. 6. As can be seen, such an envelope comprises two minimum points 51,52 that correspond to the edges of the neck of the bottle 30. By detecting such minimum points 51,52 and analysing only the intermediate measurement contributions between such minimum points 51,52 it is ensured that all of the measurements used are actually linked to the inside of the top space of the container. Downstream of the detector a signal conditioning element 40 is also connected. The signal conditioning element 40 is adapted for receiving the single measurement contributions detected by the detector, to identify for each measurement contribution a characteristic background function of the measurement conditions and to subtract such a background function from the detected signal contribution in order to extract an absorption line from which to derive the total and/or partial pressure information of the gas under examination.

In the illustrated example, the means 41 for identifying signal contributions useful for the pressure measurement are implemented in the signal conditioning element 40.

The signal conditioning element 40 preferably comprises a sub-element 42 for identifying and varying the amplitude of the detected signal contribution as a function of parameters introduced by the user, such as the type of container 30 treated, the type of gas examined and so on. The sub-element 42 for identifying and varying the amplitude of the acquired measurement signal is preferably a transimpedance circuit with automatic gain control.

The signal conditioning element 40 preferably comprises an element 43 for identifying excessively distorted measurement signal contributions in order to usefully contribute to determining the pressure measurement.

The element 43 for identifying distorted measurement signal contributions takes into account the amplitude of the absorption line extracted by each single measurement contribution relative to scanning in wavelength within the examined time period (signal acquisition sub-window), discarding the measurement contributions the absorption line of which has amplitude below a predetermined amplitude threshold that is variable as a function of parameters introduced by the user, such as the type of container 30 treated, the type of gas examined and so on.

The low signal amplitude is, indeed, usually due to disturbance factors such as the presence of external or internal droplets, defects in the wall of the container, the presence of a tab that allows the product to be opened, present in certain types of containers and so on. Such factors generally determine a strong attenuation of the signal.

In addition or alternatively, the element 43 for identifying distorted measurement signal contributions takes into account the angular coefficient of the rising front of each signal contribution acquired, eliminating the measurement contributions having an excessively distorted angular coefficient. For this purpose, the angular coefficient of the rising front of the acquired signal is compared with the angular coefficient of the rising front of the signal transmitted that therefore acts as reference. A distortion of the angular coefficient is determined in the case of variation between the two angular coefficients. The element 43 for identifying distorted measurement signal contributions proceeds to eliminate measurement contributions having an angular coefficient of the rising front greater or smaller than the reference angular coefficient (angular coefficient of the rising front of the transmitted signal) by a predetermined threshold value, for example equal to 20°. In other words, measurement contributions having an angular coefficient of the rising front outside of a range of angular coefficients considered admissible are eliminated. The range of admissible angular coefficients is a range centred on the reference angular value+/−the predetermined threshold value.

A rising front having an angular coefficient outside the range of admissible angular coefficients is, therefore, identified as excessively distorted to usefully contribute to the pressure measurement.

In order to be able to determine the overall measurement of the internal pressure based on the single measurement contributions, the signal conditioning element 40 preferably comprises a sub-element 44 for weighing the single measurement contributions as a function of the length of the optical paths travelled by the laser beam through the top space 31. It is thus possible to obtain the pressure measurement based on a weighted average that therefore takes into account the differences in length of the single optical paths.

The signal conditioning element 40 preferably comprises a compensation sub-element 45 of the contribution of gas present outside the container, adapted for carrying out a direct measurement of the external gas and s subsequent weighed subtraction of such a direct measurement on the totality of the measurement contributions.

In particular, the compensation element 45 carries out a weighing of the direct measurement as a function of the size of the top space 31 and therefore of the portion of the optical paths travelled by the laser beams outside of the container 30. The size of the top space 31 is a piece of data that is introduced initially by a user or acquired automatically by a calibration procedure.

In particular, the weighing of the direct measurement is carried out as a function of the average length of the external optical path travelled by the laser beams.

The measuring group 10 of the pressure in a container 30 is preferably comprised in an automatic filling and/or packaging plant wholly indicated with 100 and illustrated as an example in FIG. 5.

Such a line 100 comprises a first filling station 110 of containers 30, followed by a second station 120 for sealing and/or capping the containers 30. The measuring group 10 of the pressure in a container 30 is arranged downstream (directly or not) of the second station 120 for closing and/or capping the containers 30 with respect to the direction of forward motion of the containers 30 along the line 100.

The first 110 and the second 120 station have a circular configuration, in which the taps or filling valves 115 and the sealing and/or capping heads 125 are constrained to the periphery of a turntable or rotating carousel. Such stations 110,120 can for example be tool holders provided respectively with about eighty taps or filling valves 115 and with about twenty sealing and/or capping heads 125.

The containers 30 are conveyed through suitable conveying means 130, like for example a set of conveying means constrained or free on a conveyor belt or suspended, along a path of forward motion B that at least partially follows the periphery of the first 110 and of the second 120 station to subsequently pass through the measuring group 10. The operation of the measuring group 10 of the pressure in closed containers is as follows.

Initially, the measuring group 10 determines the rough acquisition time period useful for the measurement through the suitable device 14,14'.

For this purpose, according to the specific embodiment, the time period in which the top space 31 of a container is in the inspection area 20 is determined as described above.

When the container is in the inspection area 20, a gas different from the one being measured is preferably blown against it.

More preferably, a different has with respect to the one object of measurement is blown against the container 30 also when the container is at the entry of the inspection area 20.

During the acquisition time period, the laser source 11 repeatedly emits, towards the inspection area 20 in which the closed container 30 transits, a laser beam at a wavelength tunable with an absorption wavelength of a gas contained in the top space 31 of the closed container 30.

In particular, the laser beam is emitted towards the top space 31 of the container 30 that transits in the inspection area 20, and precisely, at the portion of container 30 made from optically transparent material.

The detector 12 detects the laser beams attenuated following the absorption that occurred at the top space 31 of the container 30 (measurement signal contributions) and, for each laser beam detected, provides in output data representative of an absorption spectrum of the gas object of measurement present in the top space 31.

Specifically, for each signal detected a characteristic background function of the measurement conditions is identified. Such a background function is subtracted from the detected signal contribution in order to extract an absorption line from which to derive the total and/or partial pressure information of the gas under examination.

In order to isolate the significant signal contributions for the measurement, the envelope 50 of the intensity profiles of the measurement contributions received that have passed through the container 30 during the acquisition time period are analysed in order to identify the points 51,52 corresponding to the walls of the container 30. Such points act as reference for the definition of a sub-window 53 contained between such points and preferably centred with respect to them, where the sub-window 53 represents the whole of the signal contributions actually useful for the pressure measurement.

Possible disturbances and/or signal distortions are compensated according to different methods that can be applied in combination or as alternatives.

The signal amplitude is preferably changed as a function of parameters introduced by the user, such as the type of container 30 treated, the type of gas examined and so on, in order to compensate for the variations in amplitude of the signal received.

Therefore excessively distorted measurement signal contributions are then identified and eliminated, so that the overall measurement is not excessively deteriorated by such contributions.

In particular, the measurement contributions the absorption line of which has amplitude below a predetermined amplitude threshold that is variable as a function of parameters introduced by the user, such as the type of container 30 treated, the type of gas examined and so on are discarded.

In addition or alternatively, the measurement contributions having an angular coefficient or slope of the rising front that diverges from the angular coefficient of the rising front of the transmitted signal beyond a predetermined threshold value, for example equal to 20°, are discarded.

The single measurement contributions are weighed as a function of the length of the optical paths travelled by the laser beam through the top space 31. The pressure measurement is therefore obtained based on a weighted average that takes into account the differences in length of the single optical paths.

The contribution of the gas under examination present outside the container is compensated, carrying out a direct measurement of the gas in absence of the container and subtracting such a direct measurement from the totality of the measurement contributions.

In particular, before proceeding to the subtraction, a weighing of the direct measurement is carried out as a function of the size of the top space 31 and therefore of the portion of the optical paths travelled by the laser beams outside the container 30. The size of the top space 31 is a piece of data that is introduced initially by a user or is acquired automatically by a calibration procedure.

In particular, the weighing of the direct measurement is carried out as a function of the average length of the external optical path travelled by the laser beams.

After having selected the measurement contributions that it is possible to consider for determining the overall measurement, an average of such contributions is made or alternatively certain contributions are selected on the basis of which to extrapolate the useful parameters for determining the concentration of the gas under examination and the pressure of the container. For example, in the case in which it is wished to measure the total pressure inside a container through absorption spectroscopy on a carbon dioxide line with WMS technology, the parameter of the distance of the minimum points of the second derivative of the absorption profile is extracted, in such a way obtaining a pressure measurement independent of the optical path. Such a provision proves particularly advantageous in the case of ovalisation of the bottle.

Alternatively, in the case in which the total pressure is measured through absorption spectroscopy on a water vapour line, the parameter of the area of the absorption profile obtained from the second derivative of the absorption profile is extracted, which makes it possible to obtain a parameter proportional to the temperature of the closed container containing a liquid and in this way allow a pressure measurement linked to a known temperature to be obtained.

The invention claimed is:

1. A measuring group for measuring the pressure in closed containers made from optically transparent material at least at a portion of a top space thereof, comprising
    at least one inspection area adapted for the passage of at least one portion of a top space of a closed container of said closed containers;
    at least one laser source with an optical axis for the emission of a laser beam at a wavelength tunable with an absorption wavelength of a gas contained in the top space of the closed container, the at least one laser source being positioned so as to direct the laser beam towards the at least one inspection area;

at least one detector positioned so as to detect at least one portion of the laser beam emitted by the laser source once it has travelled through the inspection area and to provide in output data representative of an absorption spectrum of said gas as a consequence of the passage of the laser beam through the inspection area;

at least one device for detecting the signal acquisition time period corresponding to the passage of said at least one portion of a top space of a closed container through the inspection area wherein the measuring group comprises a signal conditioning element connected downstream of the detector, the signal conditioning element being adapted for receiving single measurement signal contributions detected by the detector and processing each measurement signal contribution to extract an absorption line from the gas contained in the top space of the closed container, and means for identifying signal contributions useful for the pressure measurement amongst the data representative of an absorption spectrum acquired during the signal acquisition time period, wherein the means for identifying signal contributions useful for the pressure measurement comprises:

an element for the detection of a first and a second minimal point of a curve deriving from the envelope of intensity profiles of the data representative of the absorption spectrum of the gas acquired during the signal acquisition time period;

an element for determining of the distance between said first and said second minimal point; and an element for defining of a measurement sub-window contained between the first and second minimal points and centred with respect to the same, said measurement sub window defining the set of signal contributions useful for the pressure measurement, wherein the measuring group further comprises, upstream of the inspection area defined between the laser source and the detector, an entry channel configured so as to house at least the portions of container defining the respective top spaces travelling towards the inspection area, and at least one second flushing device, arranged at an entry of the entry channel, for injecting upstream of the inspection area with respect to a direction of forward motion of the closed containers a gas different from the gas contained in the top space of the closed container.

2. The measuring group according to claim 1, wherein the device for detecting the acquisition time period comprises at least one position sensor for detecting an instantaneous position of said containers and/or an element for detecting the instantaneous speed of forward motion of said closed containers.

3. The measuring group according to claim 1 comprising, upstream and/or downstream of the inspection area defined between the laser source and the detector, an exit channel configured so as to house at least the portions of container defining the respective top spaces travelling away from it the inspection area.

4. The measuring group according to claim 1 comprising at least one first flushing device for injecting into the inspection area a gas different from said gas contained in the top space of the closed container and/or at least one second flushing device to inject upstream of the inspection area with respect to a direction of forward motion of the closed containers a gas different from the gas contained in the top space of the closed container.

5. The measuring group according to claim 1, wherein the signal conditioning element comprises at least one signal processing sub-element of the group of signal processing sub-elements consisting of:

a sub-element for identifying and varying the amplitude of the acquired measurement signal contribution as a function of the input parameters;

a sub-element for identifying and eliminating excessively distorted measurement signal contributions;

a sub-element for weighing the single measurement signal contributions as a function of the length of the optical pathways travelled by the laser beam through the top space;

a sub-element for compensating a contribution of gas present outside the closed container, adapted for subtracting a direct measurement of the external gas from at least one measurement signal contribution.

6. An automatic filling and/or packaging plant for closed containers made from optically transparent material at least at a portion of a top space thereof comprising:

conveying means adapted for moving a plurality of containers forward along a forward motion path, along said forward motion path there being arranged in succession a first station for filling said containers comprising a plurality of taps or filling valves; and a second station for sealing and/or capping said containers comprising a plurality of sealing and/or capping heads, characterized in that downstream of said second sealing and/or capping station with respect to the forward motion path, there being arranged at least one measuring group according to claim 1.

7. A method for measuring the pressure in closed containers made from optically transparent material at least at a portion of a top space thereof, comprising the steps of:

conveying at least one portion of a top space of a closed container of said closed containers towards an inspection area;

emitting a laser beam at a wavelength tuneable with an absorption wavelength of a gas contained in the top space of the closed container towards the at least one inspection area;

detecting at least one portion of the laser beam that has travelled through the inspection area and supplying in output data representative of an absorption spectrum of the gas resulting from the passage of the laser beam through the inspection area;

determining a signal acquisition time period corresponding to the passage of said at least one portion of a top space of a closed container through the inspection area;

acquiring the data representative of an absorption spectrum of the gas detected during the signal acquisition time period;

wherein it comprises the steps of:

housing in an entry channel upstream of the inspection area at least the portions of container defining the respective top spaces travelling towards the inspection area, processing the data representative of an absorption spectrum to extract an absorption line from the gas contained in the top space of the closed container and identifying the representative data useful for the pressure measurement, amongst the acquired data representative of an absorption spectrum of the gas, and determining a pressure measurement based on the useful representative data, wherein the step of identifying the representative data useful for the pressure measurement comprises the steps of:

detecting a first and a second minimal point of a curve deriving from the envelope of intensity profiles of the data representative of the absorption spectrum of the gas acquired during the signal acquisition time period;

determining the distance between said first and said second minimal point; and defining of a measurement sub-window contained between the first and second minimal points and centred with respect to the same, said measurement sub-window defining the set of signal contributions useful for the pressure measurement.

8. The measuring method according to claim 7, wherein the step of determining the useful signal acquisition time period comprises:

receiving at least one piece of position data of the container detected through a position sensor and calculating the moment of entry of the top space of the closed container in the inspection area based on the at least one piece of position data received; or receiving a plurality of pieces of instantaneous forward motion speed data of the container and calculating the moment of entry of the top space of the closed container in the inspection area based on the plurality of pieces of instantaneous forward motion speed data received.

9. The measuring method according to claim 7, comprising a step of blowing a different gas with respect to that object of measurement against a container entering into and/or passing through the inspection area.

10. The measuring method according to claim 7, wherein the step of providing in output a piece of data representative of an absorption spectrum of the gas comprises:

compensating the variations in amplitude of the signal detected by varying the amplitude of the detected signal as a function of the material of the container and/or the type of gas object of measurement; and/or identifying and eliminating excessively distorted detected signals; and/or weighing the signal detected as a function of the length of the optical path travelled by the laser beam through the top space; and/or carrying out a direct measurement of the gas object of measurement in the absence of a container and subtracting such a direct measurement from the detected signal.

11. The measuring method according to claim 10, wherein the step of identifying and eliminating distorted detected signals comprises:

checking whether the amplitude of the absorption line is below an amplitude threshold; and/or checking whether the angular coefficient of the rising front of the detected signal is outside of an acceptable range of angular coefficients; and/or checking the presence of asymmetry between the rising front and the descending front of the detected signal and eliminating signals having an asymmetry higher than a threshold asymmetry considered acceptable;

checking a percentage of duty cycle of the detected signal and eliminating signals having a percentage of duty cycle outside of an acceptable duty cycle percentage range.

12. The measuring method according to claim 7, comprising the step of determining a pressure measurement based on:

a weighted average of the identified useful representative data;

the distance between the minimal points of the second derivative of an absorption profile determined by means of absorption spectroscopy with WMS technology;

the area of the absorption profile obtained from the second derivative of the absorption profile.

13. The measuring method according to claim 7, comprising the step of:

injecting into the inspection area a gas different from said gas contained in the top space of the closed container and/or injecting upstream of the inspection area with respect to a direction of forward motion of the closed containers a gas different from the gas contained in the top space of the closed container.

* * * * *